United States Patent
Steffan et al.

(10) Patent No.: US 9,029,597 B2
(45) Date of Patent: May 12, 2015

(54) METHOD FOR THE CONVERSION OF METHYLMERCAPTOPROPIONALDEHYDE FORMED FROM CRUDE ACROLEIN AND CRUDE METHYL MERCAPTAN

(75) Inventors: Martin Steffan, Darmstadt (DE); Hans Joachim Hasselbach, Gelnhausen (DE); Martin Koerfer, Kahl (DE); Harald Jakob, Hasselroth (DE); Jignesh Gangadwala, Mobile, AL (US)

(73) Assignee: Evonik Degussa GmbH, Essen (DE)

( * ) Notice: Subject to any disclaimer, the term of this patent is extended or adjusted under 35 U.S.C. 154(b) by 192 days.

(21) Appl. No.: 13/597,852

(22) Filed: Aug. 29, 2012

(65) Prior Publication Data

US 2013/0245318 A1 Sep. 19, 2013

Related U.S. Application Data

(60) Provisional application No. 61/529,019, filed on Aug. 30, 2011.

(30) Foreign Application Priority Data

Aug. 30, 2011 (DE) .......................... 10 2011 081 828

(51) Int. Cl.
*C07C 319/12* (2006.01)
*C07C 319/20* (2006.01)
*C07C 319/28* (2006.01)

(52) U.S. Cl.
CPC .............. *C07C 319/12* (2013.01); *C07C 319/20* (2013.01); *C07C 319/28* (2013.01)

(58) Field of Classification Search
CPC ..................................................... C07C 319/12
USPC ................... 562/531, 559; 422/187
See application file for complete search history.

(56) References Cited

U.S. PATENT DOCUMENTS

| | | | |
|---|---|---|---|
| 5,990,349 A * | 11/1999 | Geiger et al. | 562/559 |
| 6,126,972 A | 10/2000 | Körfer et al. | |
| 6,140,536 A | 10/2000 | Hasseberg et al. | |
| 6,150,563 A | 11/2000 | Hasselbach et al. | |
| 6,287,627 B1 | 9/2001 | Binder et al. | |
| 6,797,827 B2 | 9/2004 | Körfer et al. | |
| 7,119,228 B2 | 10/2006 | Buss et al. | |
| 7,179,938 B2 | 2/2007 | Weckbecker et al. | |
| 7,199,270 B2 | 4/2007 | Möller et al. | |
| 7,655,072 B2 * | 2/2010 | Hasselbach et al. | 95/235 |
| 7,833,508 B2 | 11/2010 | Redlingshöfer et al. | |
| 2005/0137426 A1 | 6/2005 | Moller et al. | |
| 2006/0016334 A1 | 1/2006 | Hasselbach et al. | |
| 2009/0018370 A1 | 1/2009 | Fukuoka et al. | |
| 2012/0165573 A1 | 6/2012 | Finkeldei et al. | |
| 2012/0215021 A1 | 8/2012 | Buss et al. | |
| 2012/0215022 A1 | 8/2012 | Buss et al. | |
| 2013/0231501 A1 | 9/2013 | Hasselbach et al. | |

FOREIGN PATENT DOCUMENTS

| | | |
|---|---|---|
| DE | 26 40 592 A1 | 3/1978 |
| DE | 197 16 373 A1 | 10/1998 |
| DE | 103 59 636 A1 | 7/2005 |
| EP | 1 978 007 A1 | 10/2008 |
| EP | 1978007 A1 * | 10/2008 |

OTHER PUBLICATIONS

U.S. Appl. No. 14/067,098, filed Oct. 30, 2013, Finkeldei, et al.
International Search Report and Written Opinion issued Dec. 3, 2012, in PCT/EP2012/066376 filed Aug. 23, 2012, with English translation of category of cited documents.
U.S. Appl. No. 13/927,430, filed Jun. 26, 2013, Zacchi, et al.
U.S. Appl. No. 09/412,135, filed Oct. 8, 1999, Bönig, et al.
U.S. Appl. No. 14/227,418, filed Mar. 27, 2014, Buss, et al.

* cited by examiner

*Primary Examiner* — Yong Chu
(74) *Attorney, Agent, or Firm* — Oblon, McClelland, Maier & Neustadt, L.L.P.

(57) ABSTRACT

A reactive rectification column suitable for the production of 2-hydroxy-4-methylmercaptobutyric acid and/or methionine contains a weir having a height of 100 mm or more.

15 Claims, 3 Drawing Sheets

METHOD FOR THE CONVERSION OF METHYLMERCAPTOPROPIONALDEHYDE FORMED FROM CRUDE ACROLEIN AND CRUDE METHYL MERCAPTAN

BACKGROUND OF THE INVENTION

1. Field of the Invention

The invention relates to a reactive rectification column, preferably for conversion of methylmercaptopropionaldehyde prepared from crude acrolein and crude methyl mercaptan to 2-hydroxy-4-methylmercaptobutyric acid and/or methionine, and to the use thereof in a method for the production of 2-hydroxy-4-methylmercaptobutyric acid and/or methionine.

2. Discussion of the Background

For the synthesis of acrolein, several routes are conceivable in principle. The background art utilizes the condensation of formaldehyde and acetaldehyde, or else the dehydration of glycerol. A further customary process which is dominant on the industrial scale is the partial oxidation of propene. For preparation of acrolein, the reaction is performed in a conventional process, for example in a shell-and-tube reactor filled with a catalyst. The heterogeneously catalysed oxidation of propene forms not only the acrolein target product but also further secondary components, principally acrylic acid and carbon oxides ($CO$, $CO_2$). Further secondary components are in particular acetaldehyde, formaldehyde, propionaldehyde, unsaturated organic acids, ketones and water (see U.S. Pat. No. 6,057,481 and DE 1 618 889). The reaction gas comprising the acrolein is therefore first scrubbed with water or with a water-solvent mixture in order to free it of high-boiling compounds such as acrylic acid and acetic acid, and polymer residues. Introduction of the cleaned reaction gas into cold water gives an aqueous acrolein solution. Uncondensable gases such as $N_2$, excess propene and any propane (according to the propene quality), $CO$ and $CO_2$ leave the absorber via the top and can in some cases be used as an inertization medium in the reaction section. The remaining components of the offgas are sent to an incineration plant. The crude acrolein purified to free it of high-boiling compounds and uncondensable gases is obtained from the aqueous acrolein solution under reduced pressure and at elevated temperatures, and suitable stabilizers, for example hydroquinone, are added to counteract polymerization.

The background art specifies acetaldehyde and water as secondary components which are formed in the preparation of acrolein and are present in the crude acrolein. Distillation of the crude acrolein is possible, but crude acrolein purified by distillation would still contain traces of acetaldehyde. If the crude acrolein were then to be reacted with methyl mercaptan (MC) to give 3-methylmercaptopropionaldehyde (MMP), the background art (U.S. Pat. No. 6,057,481, DE 1 618 889) states that acetaldehyde (and other volatile secondary components) are removed from the crude acrolein advantageously only after it is converted to MMP. The reason for this is that the volatile acrolein is then converted to a high-boiling component and can thus be separated more easily from acetaldehyde or low boilers in general, and these components do not adversely affect the synthesis of 3-methyl-mercaptopropionaldehyde from acrolein and methyl mercaptan. The same applies, as already described in DE 103 59 636 A1, to the use of crude methyl mercaptan from which, after reaction with acrolein to give 3-methylmercaptopropionaldehyde, the unconverted $H_2S$ and methanol reactants can be removed more easily.

It has additionally been stated that the crude acrolein, in addition to the known compounds such as acetaldehyde, may also contain traces of allyl alcohol (see Ullmann's Enzyklopädie der technischen Chemie, Weinheim 2007, "Acrolein and Methacrolein" chapter, section 4, page 10). Studies by the inventors have now found that further unsaturated compounds such as allyl acrylate, allyl acetate and benzaldehyde may likewise be present, which are obtained as by-products of the partial oxidation of propene over a heterogeneous catalyst. The allyl components, especially allyl alcohol, even after the reaction of the crude acrolein with methyl mercaptan in the presence of a catalyst to give 3-methylmercaptopropionaldehyde and the subsequent workup (see DE 103 596 36 A1), are not completely removed and can accumulate in downstream processes, especially in the conversion of 3-methylmercaptopropionaldehyde via methylmercaptopropionaldehyde cyanohydrins to methionine (or else to 2-hydroxy-4-methylmercaptobutyric acid (MHA)). In Example 24 of U.S. Pat. No. 5,905,171, it is likewise stated that, after reaction of acrolein which originates from the catalytic oxidation of propene with MC to give MMP, allyl alcohol is present in the final product. However, it is not stated how this component is removed again from the product in the downstream processes to give methionine and/or MHA or discharged from the process.

Studies by the inventors have confirmed that the accumulation, especially of allyl alcohol, occurs in the top section of the column in which the alkaline hydrolysis (e.g. EP 2 133 329 A2 or EP 0 780 370 A2) of 5-(2-methylmercaptoethyl) hydantoin takes place (see formula III). However, discharge of the unwanted by-products via the bottom is ruled out under the prevailing conditions, as in EP 0 780 370 A2.

However, removal of these unsaturated compounds is necessary since allylic components such as allyl alcohol basically have a higher toxicity than the corresponding saturated alkyl components thereof. The methionine and/or MHA products to be prepared from the acrolein are used as animal feed additives in modern animal nutrition. The production process therefore has to ensure that all toxic compounds are removed. From a technical point of view, accumulation of the unsaturated secondary components such as allyl alcohol additionally disrupts the downstream process steps. For example, in the process for preparing methionine, the product solution is purified after the hydrolysis over activated carbon as an adsorbent. An elevated concentration of impurities would consequently lead to an increased consumption of activated carbon and thus distinctly shorten the service life, which would lead to the production of greater amounts of waste streams and/or emissions from the plant. Due to the low concentration in the crude acrolein, a distillative separation is, however, achievable only with high capital and operating costs. Furthermore, valuable acrolein would be lost in the additional workup step, which reduces the overall yield of the process. For reasons of process reliability, a conversion of the crude acrolein and subsequent removal of the secondary components is likewise more favourable since acrolein has a much higher reactivity than the MMP conversion product. The consequence thereof is an increased plant availability since a distillation of more highly concentrated acrolein can lead to deposits in different apparatuses or pipelines, which would entail intensive purification steps and an increased number thereof.

SUMMARY OF THE INVENTION

A technical object of the invention was therefore to provide a process which enables removal of unsaturated secondary components, especially of allyl alcohol, from the preparation process of methionine and/or MHA.

This and other objects have been achieved by the present invention the first embodiment of which includes a reactive rectification column, comprising:
 a weir having a height of 100 mm or more;
 wherein said reactive rectification column is suitable for production of a methionine salt.

The present invention further relates to the above reactive rectification column, further comprising: a plate;
 wherein
 the weir height is in the range from 100 to 1000 mm
 a plate spacing is in the range from 500 to 1000 mm,
 the ratio of column diameter to weir length is in the range from 1.1 to 1.3,
 a ratio of a cross-sectional area of the column to an area through which a gas flows is in the range from 1.5 to 2, and
 the number of plates is in the range from 15 to 25.

In another embodiment, the present invention relates to a method for continuous production of a methionine salt, comprising:
 producing said methionine salt in the above reactive rectification column.

The method of the present invention also comprises in one embodiment
 reacting 3-methylmercaptopropionaldehyde and hydrogen cyanide or a component that can be produced therefrom, thereby obtaining a solution containing 5-(2-methylmercaptoethyl)-hydantoin;
 alkaline hydrolysing the 5-(2-methylmercaptoethyl)-hydantoin to a methionine salt in said reactive rectification column, wherein only the solution containing 5-(2-methylmercaptoethyl)-hydantoin is fed on a topmost plate of the reactive rectification column and an alkaline circulating solution is fed on a plate located under the topmost plate.

DETAILED DESCRIPTION OF THE INVENTION

Figure 1:
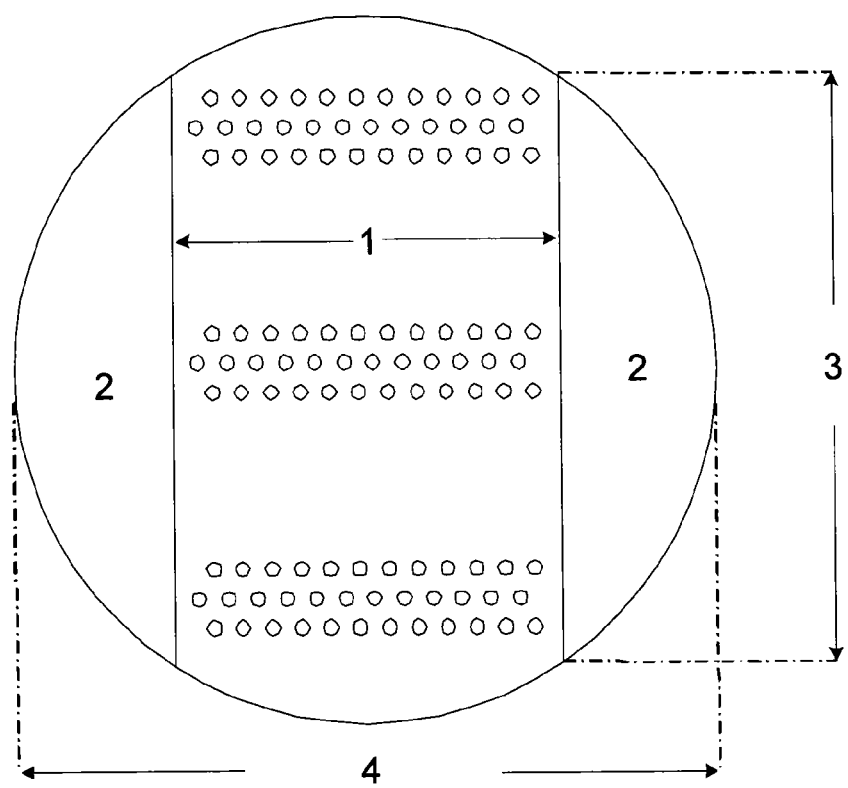
FIG. 1, top, shows a schematic top view of a sieve plate and, bottom, in one section, the side view of a column of a preferred embodiment.
Figure 1:
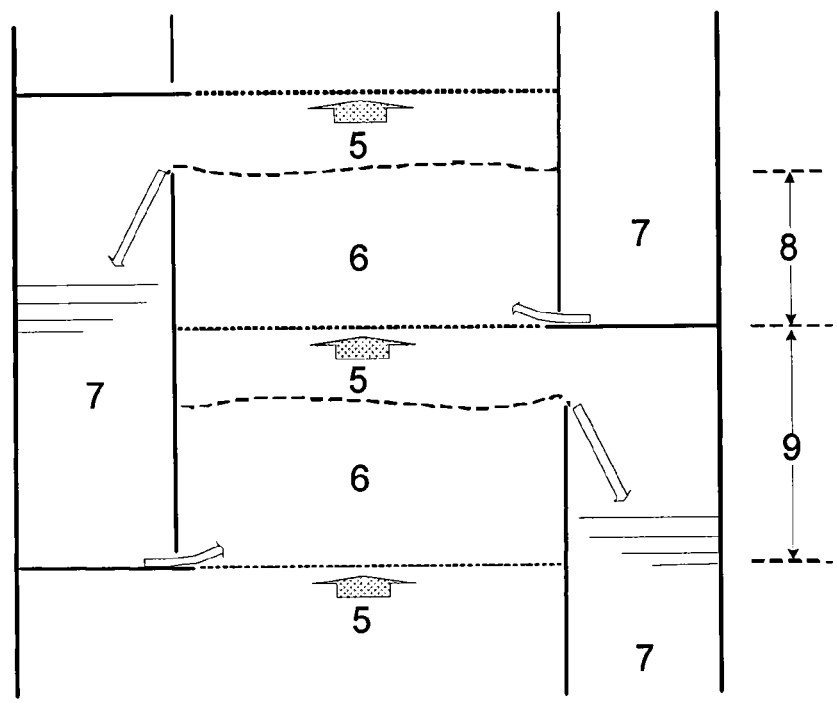

The ranges stated below include all values and subvalues between the upper and lower limit of the ranges.

The removal of the unsaturated secondary components, especially allyl alcohol, after the conversion of the acrolein to methionine and/or MHA is particularly advantageous. It was found that the alkaline hydrolysis of the methionine precursor in the inventive reactive rectification column is particularly suitable for removal of the allyl components, especially allyl alcohol, from the reaction mixture. The hydrolysis can be described as a combination of steam distillation and hydrolysis reaction which takes place at the same time.

The invention relates to a reactive rectification column (also called reactive distillation column or reactive distillation) with a weir height of 100 mm or more and to a method for the continuous production of a methionine salt using the column according to the invention.

A preferred embodiment has the following design features:
 Weir height 8: 100-1000 mm, preferably 150-700 mm
 Plate spacing 9: 500-1000 mm
 Ratio: column diameter 4/weir length 3: 1.1-1.3
 Ratio: cross-sectional area/area through which gas flows: 1.5-2
 Number of plates: 15-25, especially 18-20.

The cross-sectional area can be calculated from the column diameter 4. The area through which gas flows is found by subtracting the areas of the two downcomers (2) from the cross-sectional area.

Reference is made expressly to the preferred embodiments of the invention. The invention relates in particular to:
 1. Reactive rectification column for production of a methionine salt, wherein the weir height is 100 mm or more.
 2. Reactive rectification column according to 1, wherein
  the weir height is in the range from 100 to 1000 mm, preferably in the range from 150 to 700 mm,
  the plate spacing is in the range from 500 to 1000 mm,
  the ratio of column diameter to weir length is in the range from 1.1 to 1.3,
  the ratio of the cross-sectional area to the area through which gas flows is in the range from 1.5 to 2 and
  the number of plates is in the range from 15 to 25, preferably in the range from 18 to 20.
 3. Reactive rectification column according to 1 or 2, wherein the reactive rectification column is a sieve plate column, perforated plate column, valve plate column or bubble plate column.
 4. Reactive rectification column according to 1 to 3, wherein
  the ratio total area of all holes/area through which gas flows is in the range from 0.04 to 0.08 and
  the diameter of the individual holes in the sieve plate is in the range from 5 to 10 mm.
 5. Reactive rectification column according to 1 to 4, wherein the weir heights ensure an average residence time of the respective mixture of less than 0.5 min per plate.
 6. Reactive rectification column according to 1 to 5, wherein zirconium is used as material for parts in contact with the product.
 7. Use of a reactive rectification column according to 1 to 6 for the production of methionine.

The cross-sectional area can be calculated from the column diameter 4. The area through which gas flows is found by subtracting the areas of the two downcomers 2 from the cross-sectional area.

If the column is a sieve plate column (see FIG. 1), the following features are preferred:
Ratio: total area of all holes/area through which gas flows: 0.04-0.08
Diameter of the individual holes in the sieve plate 5-10 mm.

FIG. 1, top, shows a schematic top view of a sieve plate and, bottom, in one section, the side view of a column of a preferred embodiment. The side view shows the vapour phases 5, liquid/vapour phases 6 and the liquid phases 7 on the individual plates.

According to the invention, in addition to water, ammonia ($NH_3$) and $CO_2$, the undesired allyl components are preferably also distilled off at the top. In a particular embodiment, all of the $NH_3$ or a proportion thereof is then condensed and used in hydantoin synthesis. The stream from the bottom of the reactive distillation system contains the alkali metal salt, preferably the potassium salt of methionine, which is processed further to methionine as is known in the background art, and/or MHA.

The heating and stripping medium used is preferably steam, which is fed in under pressure below the bottommost sieve plate. The amount, velocity and temperature of the stream of steam are preferably controlled in such a way that a temperature of 180° C.-190° C. is reached at the outlet of the reactive distillation column, whereas the gas phase leaves at the top of the column at a temperature of 160° C.-170° C. This temperature range corresponds to a pressure range of 8-10 bar (gauge). Furthermore, the amount of steam depends on the desired throughputs.

The plate spacing can preferably be adjusted to the different reaction phases in the column. In one embodiment, in the top half of the column the plate spacing and the weir heights are preferably kept small, to speed up the stripping of $NH_3$ and $CO_2$, whereas in the bottom half the plate spacing and weir heights are larger, for completing the conversion with a longer residence time.

In a preferred embodiment the weir height for the upper plates of a column is in the range from 100 to 200 mm, preferably 150 mm, at a plate spacing in the range from 800 to 1000 mm, preferably 1000 mm, and the weir height for the middle plates is in the range from 400 to 600 mm, preferably 500 mm, at a plate spacing in the range from 700 to 900 mm, preferably 800 mm, and the weir height for the bottom plates is in the range from 600 to 800 mm, preferably 700 mm, at a plate spacing in the range from 800 to 1000 mm, preferably 1000 mm. The plate spacing is in each case measured from one plate to the plate below it. In the case of columns with 15 to 17 plates, preferably plates 1 to 4 count as the top plates, plates 5 to 11 as the middle plates and the lower plates count as the bottom plates. In the case of columns with 18 to 21 plates, preferably plates 1 to 5 count as the top plates, plates 6 to 12 as the middle plates and the lower plates count as the bottom plates. In the case of columns with 22 to 25 plates, preferably plates 1 to 7 count as the top plates, plates 8 to 16 as the middle plates and the lower plates as the bottom plates.

The patent application further relates to a method for continuous production of a methionine salt. The method according to the invention is especially suitable for the alkaline hydrolysis of 5-(2-methylmercaptoethyl)hydantoin to give a methionine salt, the 5-(2-methylmercaptoethyl)hydantoin having been produced from 3-methylmercapto-propionaldehyde and hydrogen cyanide (HCN) or a component that can be produced therefrom. In a preferred embodiment of the method, only a solution containing 5-(2-methylmercaptoethyl)-hydantoin is fed on the topmost plate of the reactive rectification column, while an alkaline circulating solution is fed on a plate located under that, preferably on the 2nd plate from the top. The alkaline circulating solution preferably contains an alkali metal carbonate, preferably potassium carbonate.

The invention relates in particular to a
1. Method for continuous production of a methionine salt, wherein the method is carried out in a reactive rectification column according to invention.
2. Method according to 1, wherein the following steps are carried out:
    reaction of 3-methylmercaptopropionaldehyde and hydrogen cyanide or of a component that can be produced therefrom, wherein a solution containing 5-(2-methylmercaptoethyl)-hydantoin is obtained;
    alkaline hydrolysis of the 5-(2-methylmercaptoethyl)-hydantoin obtained to a methionine salt in a reactive rectification column, wherein only the solution containing 5-(2-methylmercaptoethyl)-hydantoin is fed on the topmost plate of the reactive rectification column and an alkaline circulating solution is fed on a plate under that, preferably on the 2nd plate from the top.
3. Method according to 2, wherein the alkaline circulating solution contains an alkali metal carbonate, preferably potassium carbonate.
4. Method according to 1 to 3, wherein allyl components, especially allyl alcohol, are removed at the top of the reactive rectification column.
5. Method according to 1 to 4, wherein water, ammonia and $CO_2$ are removed from the top of the reactive rectification column and the $NH_3$ removed is condensed completely or partially for use in the synthesis of 5-(2-methyl-mercaptoethyl)-hydantoin.
6. Method according to 1 to 5, wherein the concentration of ammonia in the bottom of the rectification column is less than 120 ppm, preferably less than 100 ppm and most preferably less than 80 ppm.
7. Method according to 1 to 6, wherein the alkaline hydrolysis is carried out at a temperature in the range from 160° C. to 190° C.
8. Method according to 7, wherein the temperature of the reaction mixture at the outlet of the reactive rectification column is in the range from 180° C. to 190° C.
9. Method according to 7 or 8, wherein the temperature of the gas phase at the top of the reactive rectification column is in the range from 160° C. to 170° C.
10. Method according to 1 to 9, wherein alkaline hydrolysis is carried out at a pressure in the range from 8 bar (gauge) to 10 bar (gauge).
11. Method according to 1 to 10, wherein steam is used as heating and stripping medium in the reactive rectification column.

Preferred starting substances for the production of 5-(2-methylmercaptoethyl)-hydantoin (also called hydantoin derivative or hydantoin for short) are 3-methyl-mercaptopropionaldehyde, hydrogen cyanide, ammonia and carbon dioxide. By-products of this reaction are the components 5-(2-methylmercaptoethyl)-hydantoic acid amide, 5-(methylmercaptoethyl)-hydantoic acid, methionine amide and in traces, along with other components, 3-methylmercaptopropionaldehyde cyanohydrin. These can be converted to methionine in alkaline hydrolysis, just like the main product. An exception is 3-methylmercaptopropionaldehyde cyanohydrin, which on hydrolysis is converted to 4-methylmercapto-2-hydroxybutanoic acid. The precise composition of the product mixture produced in the hydantoin reaction can be elucidated by HPLC.

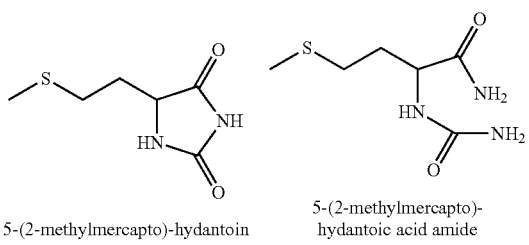

5-(2-methylmercapto)-hydantoin     5-(2-methylmercapto)-hydantoic acid amide

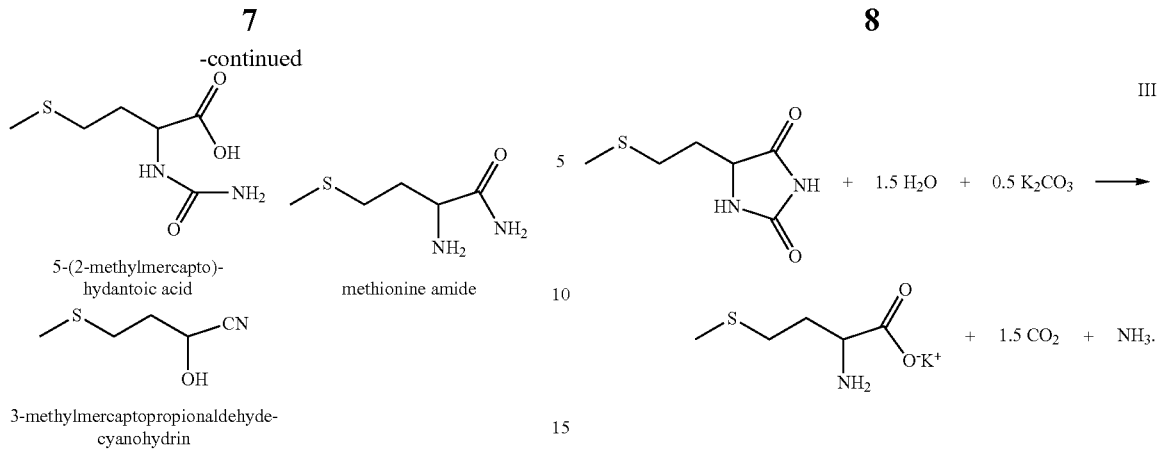

5-(2-methylmercapto)-
hydantoic acid methionine amide 3-methylmercaptopropionaldehyde-
cyanohydrin Alternatively, in hydantoin production it is also possible to use previously synthesized MMP-cyanohydrin.

For complete conversion of MMP to the hydantoin derivative, it is advantageous if MMP and $NH_3$ are used in the reactive absorber in a molar ratio of about 1 to 3, wherein the basic equation of hydantoin synthesis has the following appearance (formula I):

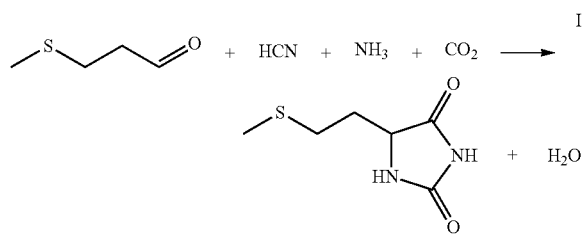

In a subsequent step, the hydantoin derivative is converted in alkaline hydrolysis to methionine. Methionine denotes racemic methionine, which is also designated as D,L-methionine. This step of the method according to the invention is preferably carried out in a sieve plate column, which is operated as reactive distillation.

The reaction to give 4-methylmercapto-2-hydroxybutanoic acid (=methionine hydroxy analogue, MHA) proceeds according to the following reaction equation.

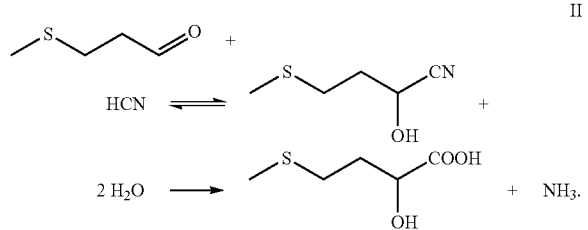

The reactive distillation column that is operated in the method of the invention, and is preferably equipped with sieve plates, brings about—along with very effective distillation of the ammonia—mainly a very advantageous reaction for alkaline hydrolysis of hydantoin with formation of the potassium salt of methionine. This takes place according to formula III.

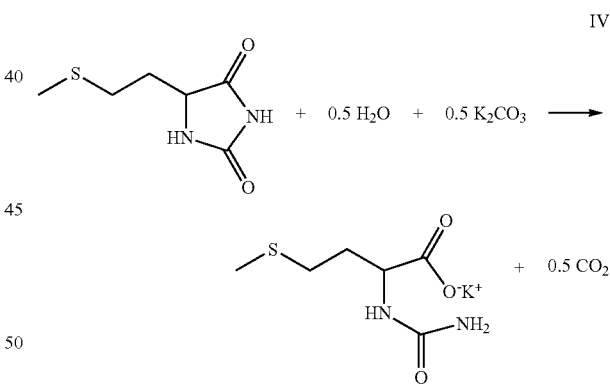

The reactive rectification column according to the invention is preferably operated in a reactive distillation-reactive absorber coupled system. The amount of $HN_3$ required for this purpose does not have to be prepared and fed in separately, but is circulating in the system. The concentration of ammonia in the bottoms product is preferably less than 120 ppm, more preferably less than 100 ppm and most preferably less than 80 ppm. This manner of operation means that it is advantageously possible in the "steady state" to dispense with external $NH_3$ feed completely.

It has been found that when hydantoin hydrolysis is carried out in reactive distillation designed as a sieve plate column, several advantageous effects can be achieved.

The inventors' own intensive research into the reaction mechanism of hydantoin hydrolysis showed, surprisingly, that first there is formation of a stable intermediate, namely the potassium salt of hydantoic acid, according to the following equation (formula IV).

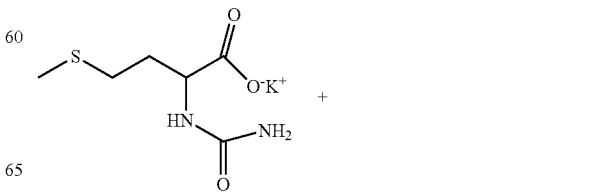

The further hydrolytic degradation of hydantoic acid takes place according to the following equation (formula V):

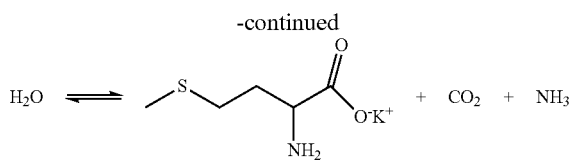

As the potassium salt that has formed can react via the equilibrium reaction back to the salt of hydantoic acid, for conversion that is as complete as possible, with short reaction times as are required industrially, it is a considerable advantage if, in addition to the allyl components, ammonia and $CO_2$ are also removed effectively from the liquid phase during the reaction. A sieve plate column is used for this in one embodiment.

The preferred combination of reactive rectification column and reactive absorber permits the provision of process conditions that make the production of methionine quite particularly economically attractive. For controlling a stable $NH_3$ holdup in the reactive distillation-reactive absorber system, in a further embodiment a small partial stream can be deliberately taken from the gaseous top product and discarded. In this way, the excess $NH_3$ that forms can be removed from the system in an environment-friendly manner and avoiding loss of valuable raw materials.

The reactive rectification column can have sampling points on one or more or all plates. Preferably it has sampling points on every fourth, every third, every second to fourth or third, especially preferably on every second plate. The samples taken are preferably allowed to cool and are analysed for hydantoin, hydantoic acid, methionine, methionyl-methionine by high-performance liquid chromatography (HPLC). The $NH_3$ content can be determined potentiometrically by means of an ion-selective electrode.

The preferred embodiment of reactive distillation equipped with sieve plates (see FIG. 1) can be operated with an amount of steam of less than 0.25 t steam per t process solutions, fed at the top of the column. This is completely unexpected, because at the high pressures in reactive distillation described above and the aforementioned large $NH_3$ circulation, when using a reactive distillation-reactive absorber system, from the top of reactive distillation of about 0.4 t $NH_3$ per t of MMP employed, much larger $NH_3$ losses via the bottom of the column were to be expected. A lower limit is imposed for the amount of steam used when the so-called weep point of the sieve plates is reached. This is understood as the effect that starting from a certain reduced gas flow from below, liquid is increasingly discharged (weeps) directly through the holes of the sieve plates and no longer takes the intended path via the downcomers 2. As a result, the residence time for the hydrolysis reaction would be lost and thus a desired function of reactive distillation would be disturbed. In detailed studies of the present reaction system it was determined that the weep point is equal to 50% of the specific amount of steam stated above. The preferred amounts of steam are in the range from 0.13 t steam per t process solution to 0.4 t steam per t process solution, most preferably in the range from 0.20 t steam per t process solution to 0.25 t steam per t process solution.

In a preferred embodiment, zirconium is used in the reactive distillation and/or in the reactive absorber and/or in the second reactor as material for the parts in contact with the product. As a result, corrosion damage to the parts in contact with the product can be avoided sustainably. The possible process combination of reactive distillation and reactive absorption proves particularly advantageous, against the background that zirconium is a high-cost material, because the close coupling of the two process steps minimizes the number and length of connecting pipelines and the number of buffer tanks. Accordingly, the method of the invention is on the whole very sustainable, as it avoids the discharge of environmentally harmful heavy metals such as chromium and nickel due to corrosion. Furthermore, the close coupling of the process steps means that the waste heat resulting from operation of the column can be utilized ideally for warming the feed streams and additionally for operation of the evaporating unit.

The reaction system according to the invention ensures a sufficient residence time of the reaction partners in the column. At the same time, in view of the high costs of the material zirconium, it is advantageous if the number of plates can be kept small. The plates are preferably sieve plates. Other usual plate designs (e.g. slotted, valve or bubble-cap plates) can be used, but they have the disadvantage that manufacture thereof from the material zirconium is very difficult. Therefore in this application reference is made to sieve plates and sieve plate columns. The invention is not, however, limited to these, but relates equally to slotted, valve or bubble-cap plates or slotted, valve or bubble-cap plate columns, unless expressly stated otherwise.

In one embodiment the reactive distillation column provides quantitative hydrolysis of hydantoin at temperatures between 160° C. and 180° C. in the pressure range 8 bar (gauge) to 10 bar (gauge) in a residence time of less than 10 minutes, wherein the column ensures an average residence time of less than 0.5 minute per plate. The weir height has an important influence on the residence time of the individual sieve plate (see FIG. 1). It was found, surprisingly, that far larger weir heights are possible in the reaction system of the invention than those described in the background art (see e.g. Mersmann, Thermische Verfahrenstechnik (Thermal process engineering), p. 222, Springer Verlag, 1980). Weir heights up to max. 60 mm are stated in the latter, whereas weir heights up to 1000 mm are used in the invention. Therefore in a preferred embodiment the use of zirconium as material is minimized, while simultaneously reducing the $NH_3$ concentration at column outlet to less than 100 ppm.

The mother liquor from precipitation of the methionine salt is preferably used for the alkaline hydrolysis of hydantoin. The mother liquor contains the potassium salts mainly as $KHCO_3$. These are then preferably concentrated, to remove $CO_2$ and water, which leads to a solution with high potassium carbonate content and therefore increased basicity, which is advantageous for the hydrolysis reaction.

The energy required for operation of this evaporation step can be obtained in an especially suitable manner from the waste heat of the reactive distillation-reactive absorption combination. In a preferred embodiment, the amount of water that is required for production of the amounts of steam necessary for operation of the reactive distillation is obtained from the condensate of the evaporation step. In this way the complete methionine production process can be operated largely without generating wastewater, which represents a considerable advantage from the environmental standpoint.

In a preferred embodiment, for alkaline hydrolysis, the reaction solutions are introduced into the reactive rectification column in such a way that only the solution containing 5-(2-methylmercaptoethyl)-hydantoin is fed in at the topmost plate and the alkaline potassium circulating solution is fed on a plate located under that, preferably on the 2nd plate from the top. Therefore first preferably $NH_3$, $CO_2$ and HCN are stripped from the hydantoin solution and recycled to the hydantoin reaction. As a result, in particular the loss of HCN according to formula VI is minimized and at the same time formation of potassium formate is avoided. Potassium formate, as a neutral salt, is not suitable for supporting the hydrolysis of hydantoin and must therefore be extracted from the potassium circuit. The associated losses of potassium must be made up using KOH. The sequential feed of hydantoin solution and alkaline potassium circulating solution at the top of the reactive distillation column therefore avoids costs for raw materials and waste disposal.

$$HCN + 2H_2O \rightarrow NH_3 + HCOOH \qquad \text{VI}$$

In a preferred embodiment, using a reactive distillation column with sieve plates, advantageously the formation of by-products such as methionine dipeptide is suppressed. Since formation of methionine dipeptide requires the simultaneous presence of the starting compound hydantoin and the potassium salt of methionine, efficient separation of the reaction partners is advantageous for avoiding this reaction. This takes place in an especially suitable manner in a reactive distillation equipped with sieve plates, as remixing is largely prevented in this system. However, the invention is not restricted to this, but relates equally to slotted, valve or bubble-cap plates or slotted, valve or bubble-cap plate columns, unless expressly stated otherwise. In this way, the proportions present in the hydrolysed reaction mixture are 98 mol. % Met and 2 mol. % Met-dipeptide, wherein a residence time of less than 10 minutes is required.

The preferred method of the invention of alkaline hydantoin hydrolysis in a sieve plate column minimizes the formation of the by-product Met-dipeptide by exploiting two synergistic effects. On the one hand, the plate design largely prevents remixing and as a result formation of Met-dipeptide is inhibited, and on the other hand the intensive stripping operation increases the basicity in the reaction solution, as shown by the following reaction equation.

$$CO_3^{2-} + H_2O \rightarrow 2OH^- + CO_2, gas \qquad \text{VII}$$

An increased proportion of base in its turn accelerates cleavage of the resultant Met-dipeptide. The mechanism is shown in formula VIII:

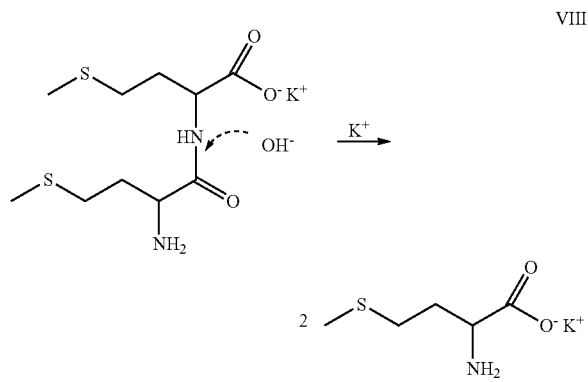

This explains how the multi-stage sieve plate column of the invention both minimizes Met-dipeptide formation and supports the hydrolytic degradation of the dipeptide, which overall greatly reduces the losses associated with by-product formation and disposal thereof.

The presence of a sufficient amount of non-volatile basic compounds in the reaction matrix is important for efficient conversion of hydantoin to methionine in the column of the invention. These are potassium salts, such as KOH, potassium carbonate, potassium hydrogen carbonate, potassium-methionine, potassium salt of Met-dipeptide. As these potassium salts are very largely recycled, but at the same time potassium salts of strong acids are also formed in side reactions, it is important to monitor the basicity in the potassium circuit and keep it stable.

In the continuous process of the invention it is therefore important to determine the basicity, in particular at column outlet. For this, a sample is taken and after it has cooled to ambient temperature it is submitted to classical acid-base titration. Preferably, the pH of the reaction mixture at the outlet of the column is in the range from 4 to 5. Preferably the basicity values in the reaction matrix at the end of the reaction are in the range from 2.2-2.8 mol base per kg saponified solution, preferably 2.5 mol base/kg saponified solution. Lower basicities lead to increased Met-dipeptide formation and higher $NH_3$ concentrations in the saponified product. Higher basicity values mean that, relative to the amount of Met produced, increased circulation of alkaline potassium salts is required in the process. This is energetically increasingly costly and therefore counterproductive.

Having generally described this invention, a further understanding can be obtained by reference to certain specific examples which are provided herein for purposes of illustration only, and are not intended to be limiting unless otherwise specified.

EXAMPLES

Example 1

Figure 2:
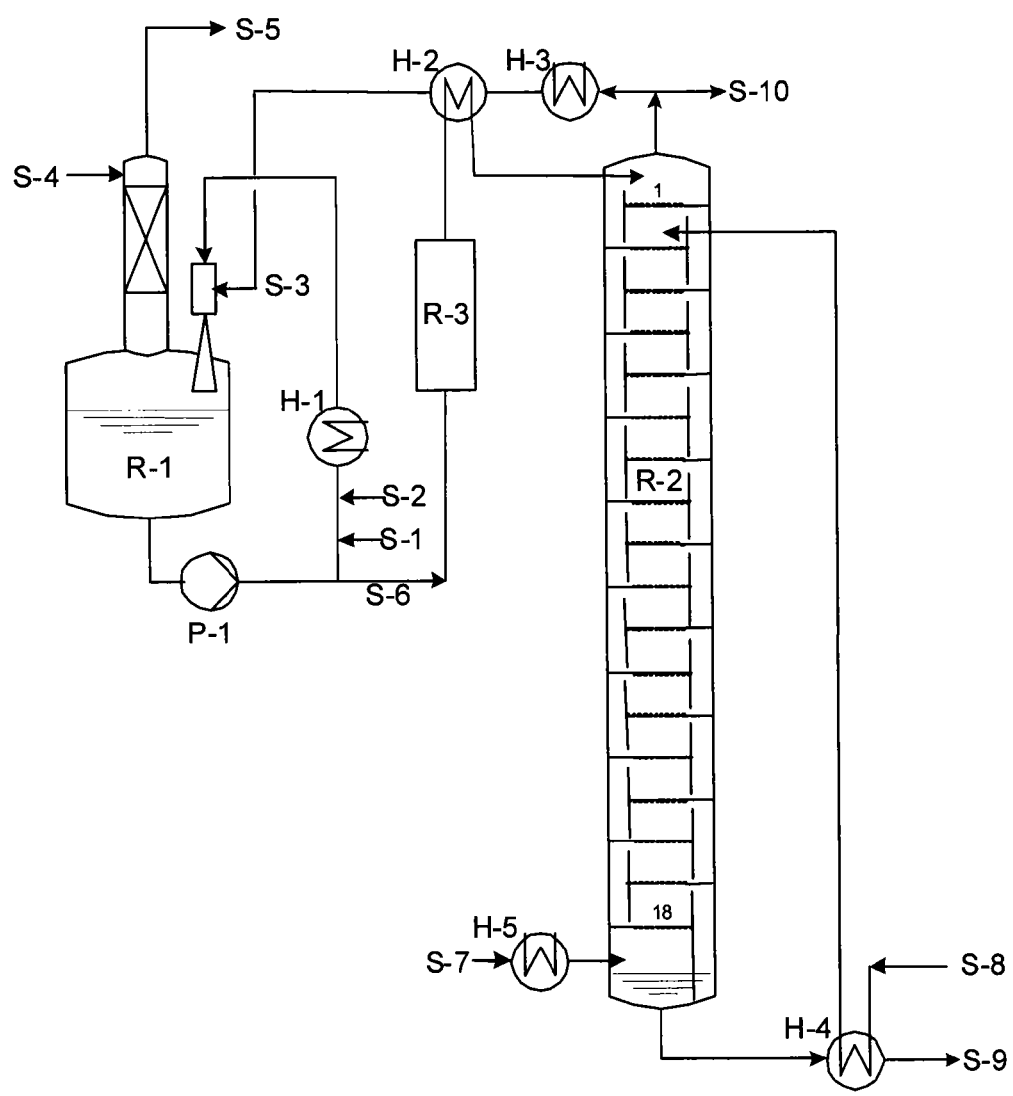
FIG. 2 shows a flow chart of a plant including a sieve plate column according to an embodiment of the invention.

FIG. 2 provides further explanation of the invention.

The production of hydantoin took place in the reaction system R-1. The raw materials HCN and MMP were mixed via the feed points S-1 and S-2 with about 20-times the amount of hydantoin reaction solution, which was circulated by pump P-1. Heat exchanger H-1 served for abstraction of heat and maintained the reactor contents R-1 preferably at a temperature of 100° C.-120° C. Alternatively, a premix of MMP and HCN or separately produced MMP-cyanohydrin could also be fed into the stream circulated by pump P-1. The resultant combined stream then served as the driving jet in a jet mixer, which brought the partially condensed low-boiling fractions (S-3) from the top of the reactive distillation R-2 intensively into contact with the hydantoin process solution and returned them to reactor R-1. Via stream S-5, which was washed with water (S-4) until $NH_3$-free, a $CO_2$-containing stream left the reactor R-1. This $CO_2$ stream arose because according to formula III, in hydantoin hydrolysis in the presence of potassium carbonate, stoichiometrically 0.5 mol more $CO_2$ forms per mol of methionine formed than was required for hydantoin formation according to formula I. The resultant $NH_3$-free $CO_2$-stream was, as described in U.S. Pat. No. 7,655,072 B2, usefully returned to the processing section for isolation of crystalline methionine, as $CO_2$ was used there for neutralizing the alkaline process solution.

The liquid hydantoin-containing stream S-6 was led via a second reactor R-3, to complete the conversion. Simultaneously, entry of MMP-cyanohydrin into the hydrolysis reactor R-2 was prevented. In order to minimize the energy required in the reactive distillation R-2, the hydantoin-containing process stream S-6 was preferably preheated to 130° C. by means of heat exchanger H-2 before entering at the topmost plate of the sieve-plate column R-2. On plate 1 of the reactive distillation, first any HCN still present was preferably expelled. This reduced the hydrolysis of the HCN to the potassium salt of formic acid that otherwise occurs in the alkaline in the reactive distillation (formula VI).

The hydrolysis of hydantoin to methionine began with the concurrence of the hydantoin-containing process solution and stream S-8, which came from the concentrated filtrates from processing to the methionine salt solids S-9. Stream S-8 took as much heat as possible from the bottoms product of reactive distillation (heat exchanger H-4) and was thus preferably heated to 170° C. By means of evaporator unit H-5, steam was preferably produced for operation of the reactive distillation, using condensates from processing (stream S-7) as the source of water.

Via stream S-10, the undesired allyl components were removed. In addition, the stream S-10 further served to regulate the ammonia balance in the coupled system of the invention, because, firstly, the use of excess HCN in hydantoin synthesis and hydrolysis thereof to $NH_3$ and formic acid, gave rise to additional amounts of $NH_3$, which could be withdrawn very selectively at this point, i.e. without losses of hydantoin or methionine. Evaporator H-3 produced, from boiler feed water, heating steam of pressure stage 3 bar (gauge) (130° C.), which was preferably used in evaporation of the methionine mother liquor. Therefore, ideally, waste heat from the reactive distillation operated at temperatures between 170° C. and 190° C. could be used in further processing, so that the complete production process for methionine according to the method of the invention was energetically extremely favourable and therefore economically attractive.

Example 2

A sieve plate column with a diameter of 1 meter and 18 sieve plates as shown in FIG. 2 was used for continuous production of methionine. The following table shows the arrangement of the sieve plates, their spacing and weir heights:

| Plate No. | Weir height [mm] | Plate spacing [mm] |
|---|---|---|
| 1 to 5 | 150 | 1000 |
| 6 to 12 | 500 | 800 |
| 13 to 18 | 700 | 1000 |

Tank R-1 was operated with a hold-up of 3 $m^3$, and the second reactor had a hold-up of 1 $m^3$. Pump P-1 provided circulation of 42 t/h. At S-1, 442 kg/h HCN (16.92 kmol/h) and at S-2, 1688 kg/h MMP (16.24 kmol/h) were fed into this stream. Via S-3, a stream of 6063 kg/h with an $NH_3$ content of 11.6 wt. % of condensates from the top of the reactive distillation was mixed into the circulated process solution. Excess $CO_2$ gas (400 kg/h) left tank R-1 via a washing column, which was fed at the top (S-4) with 770 kg/h water, so that the waste gas stream was washed until $NH_3$-free and could then be recycled.

By means of condenser H-1, the temperature at the outlet of R-1 was controlled at 105° C. The hydantoin reaction solution (S-6) was led through the second reactor R-3 for completing the reaction, it was heated in the heat exchanger H-2 to 130° C. and then fed at the topmost plate of the sieve plate column. 14.14 t/h of potassium carbonate—containing process solution (S-8), heated by heat exchanger H-4 to 170° C., containing the following components: 66 g/kg Met, 158 g/kg potassium, 48 g/kg Met-Met, 6.5 g/kg MHA, 12.5 g/kg formate, 3.6 mol base/kg for basicity, was pumped onto plate 2.

The stream of steam required for operation (5470 kg/h) was produced by evaporator H-5 (S-7) and was fed in below the bottommost sieve plate. From the stream distilled at the top, a partial stream S-10 (54 kg/h) was diverted and discarded. The amount of allyl alcohol in S-10 here was in the range from 0.5-1.7 kg/h.

The pressure at the top of the sieve plate column was 8.2 bar (gauge) and the temperature at the inlet of the heat exchanger H-3 was 165° C. The differential pressure over all sieve plates was 450 mbar.

The temperature in the bottom of the column was 189° C.

At column outlet there was a stream S-9 of 22.15 t/h, which contained the following components: 149 g/kg Met, 32 g/kg Met-Met, 101 g/kg potassium, 8.2 g/kg formate, 4.2 g/kg MHA and with a basicity of 2.5 mol base/kg.

Figure 3:
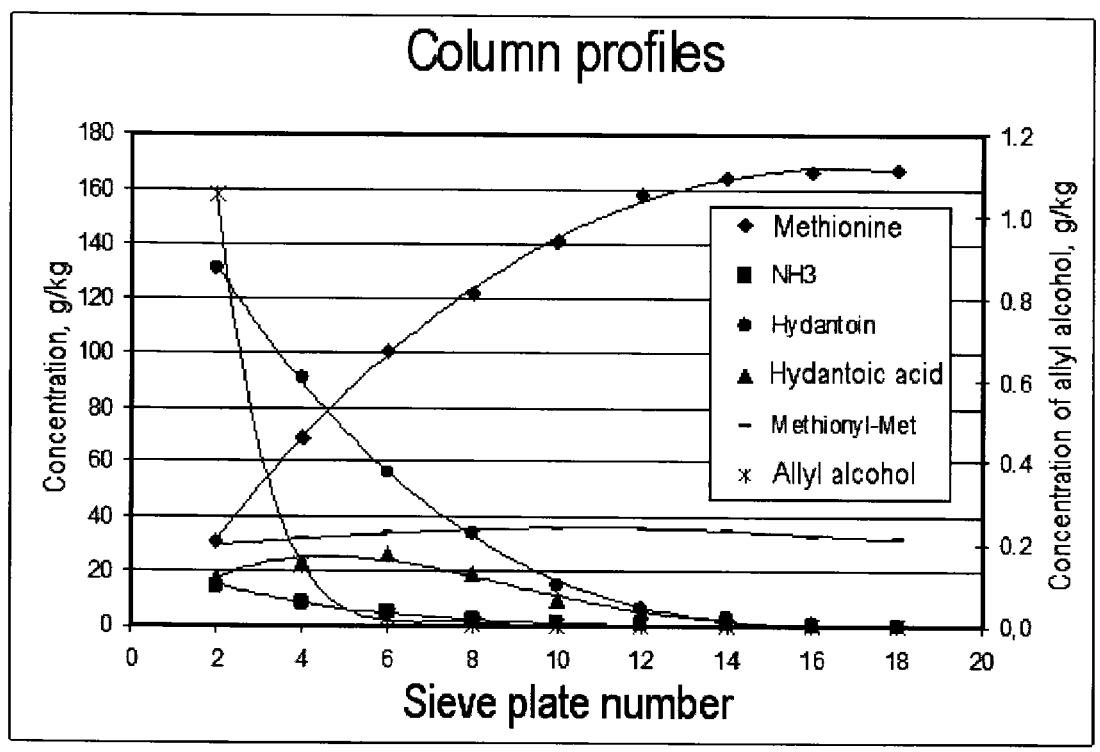
FIG. 3 shows the composition on the various sieve plates in a column of one embodiment of the invention.

The sieve plate column was equipped with sampling points on plates 2, 4, 6, 8, 10, 12, 14, 16 and 18. The samples were cooled immediately and were analysed by high-performance liquid chromatography (HPLC) for hydantoin, hydantoic acid, methionine, methionyl-methionine. The $NH_3$ content was determined potentiometrically by means of an ion-selective electrode. The concentrations of allyl alcohol were determined using an Aspen simulation. A direct analysis of the allyl alcohol was carried out in the crude AC and in the hydantoin synthesis (R-1). The composition on the various sieve plates is presented in the following table and in FIG. 3.

| Sieve plate No. | Methi-onine [g/kg] | $NH_3$ [g/kg] | Hydan-toin [g/kg] | Hydantoic acid [g/kg] | Methionyl-Met [g/kg] | Allyl alcohol* [g/kg] |
|---|---|---|---|---|---|---|
| 2 | 31 | 14.2 | 131 | 18 | 30 | 1.1E+00 |
| 4 | 69 | 8.4 | 91 | 23 | 32 | 1.5E−01 |
| 6 | 101 | 5 | 56 | 26 | 34 | 2.1E−02 |
| 8 | 122 | 2.4 | 34 | 19 | 35 | 2.8E−03 |
| 10 | 141 | 1.5 | 15.1 | 10 | 35.5 | 3.5E−04 |
| 12 | 158 | 0.7 | 6.4 | 5 | 36 | 4.5E−05 |
| 14 | 164 | 0.6 | 3.2 | 2.4 | 35 | 5.9E−06 |
| 16 | 166 | 0.2 | 1.2 | 0.6 | 33 | 7.9E−07 |
| 18 | 167 | 0.1 | 0 | 0 | 32 | 9.9E−08 |

*Data from Aspen simulation

For determining the residence time, the liquids content was determined continuously, by first stopping streams S-6, S-7, S-8 and S-9 simultaneously. After waiting until no further increase in level was recorded in the column bottom, the initial level was restored in the column bottom by pumping out. The amount of solution pumped out was 2.4 t. Since the throughput in continuous operation was 22.15 t/h, this gave a residence time of the liquid phase of 6.5 min.

U.S. provisional application 61/529,019 filed Aug. 30, 2011, and German patent application DE 102011081828.6 filed Aug. 30, 2011, are incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A method for production of a methionine salt, comprising:
introducing a solution comprising 5-(2-methylmercaptoethyl)-hydantoin to a reactive rectification column through an upper inlet;
introducing an aqueous alkaline solution through a second inlet located in an upper section of the reactive rectification column;
hydrolyzing 5-(2-methylmercaptoethyl)-hydantoin in the alkaline medium in the reactive rectification column to obtain a solution comprising the methionine salt at a bottom of the reactive rectification column;

removing the solution of the methionine salt from the rectification column through a bottom outlet of the reactive rectification column; and removing low boiling components from the alkaline hydrolysis medium from an upper outlet of the reactive rectification column;

wherein the alkaline hydrolysis medium is partially retained on a gas permeable area of plates of the reactive rectification column and volatile vapors of low boiling components rise through the column through the gas permeable area of the plates, the low boiling components removed in the upper outlet comprise allyl compounds, HCN and optionally, $NH_3$; and the reactive rectification column, comprises:

a steam supply in a bottom region of the rectification column;

from 15 to 25 vertically stacked plates having a vertical spacing between the plates of from 500 to 1000 mm;

each plate comprising an area permeable to a gas, which is less than a total cross-sectional area of the plate, a downcomer region which is not perforated, a downcomer open area and a weir having a height of from 100 to less than 1000 mm separating the area of gas permeability from the open downcomer area;

wherein the downcomer region of adjacent plates alternates to opposite portions of the cross-sectional area of the plates through the vertical order of the plates, the upper inlet through which the solution comprising 5-(2-methylmercaptoethyl)-hydantoin is introduced to the column is located above an uppermost plate of the vertical stack of plates, the inlet through which the alkaline medium is introduced to the reactive rectification column is located lower than the uppermost plate of the vertical stack of plates.

2. The method according to claim 1, further comprising:

reacting 3-methylmercaptopropionaldehyde and hydrogen cyanide or a component that can be produced therefrom, thereby obtaining the solution comprising 5-(2-methylmercaptoethyl)-hydantoin.

3. The method according to claim 1, wherein the alkaline solution which enters the second inlet comprises an alkali metal carbonate and comprises mother liquor from precipitation of methionine salt.

4. The method according to claim 1, wherein an allyl component is removed at the top of the reactive rectification column.

5. The method according to claim 1, wherein water, ammonia and $CO_2$ are removed from the top of the reactive rectification column and the $NH_3$ removed is condensed completely or partially and is employed as a reactant in the synthesis of 5-(2-methylmercaptoethyl)-hydantoin.

6. The method according to claim 1, wherein a concentration of ammonia at the bottom of the rectification column is less than 120 ppm.

7. The method according to claim 1, wherein the alkaline hydrolysis is carried out at a temperature in the range from 160° C. to 190° C.

8. The method according claim 7, wherein the temperature of the reaction mixture at the outlet of the reactive rectification column is in the range from 180° C. to 190° C.

9. The method according to claim 7, wherein the temperature of the gas phase at the top of the reactive rectification column is in the range from 160° C. to 170° C.

10. The method according to claim 1, wherein the pressure of the alkaline hydrolysis is from 8 bar(gauge) to 10 bar (gauge).

11. The method according to claim 1, wherein a heating and stripping medium in the reactive rectification column comprises steam.

12. The method according to claim 1, wherein the alkaline solution is fed on the 2nd plate from the top.

13. The method according to claim 2, wherein the alkaline solution comprises potassium carbonate.

14. The method according to claim 1, wherein allyl alcohol is removed at the top of the reactive rectification column.

15. The method according to claim 1, wherein a concentration of ammonia at the bottom of the rectification column is less than 100 ppm.

* * * * *